(12) United States Patent
Song et al.

(10) Patent No.: US 10,940,092 B2
(45) Date of Patent: Mar. 9, 2021

(54) TECHNOLOGIES FOR MEDICINE DISPENSING

(71) Applicants: Michael Moonsup Song, Old Tappan, NJ (US); Yoon Jung Song, Old Tappan, NJ (US)

(72) Inventors: Michael Moonsup Song, Old Tappan, NJ (US); Yoon Jung Song, Old Tappan, NJ (US); Ryan A. Kelly, Yorktown Heights, NY (US); Paul Dowd, Scarsdale, NY (US)

(73) Assignees: Michael Moonsup Song, Old Tappan, NJ (US); Yoon Jung Song, Old Tappan, NJ (US)

( * ) Notice: Subject to any disclaimer, the term of this patent is extended or adjusted under 35 U.S.C. 154(b) by 0 days.

(21) Appl. No.: 15/491,797

(22) Filed: Apr. 19, 2017

(65) Prior Publication Data
US 2018/0303718 A1    Oct. 25, 2018

(51) Int. Cl.
*A61J 7/00* (2006.01)
*A61J 7/04* (2006.01)
*G07F 17/00* (2006.01)
*G06F 19/00* (2018.01)
*G07F 11/00* (2006.01)
*G07F 11/44* (2006.01)
(Continued)

(52) U.S. Cl.
CPC .......... *A61J 7/0076* (2013.01); *A61J 7/0445* (2015.05); *G06F 19/3462* (2013.01); *G07F 11/005* (2013.01); *G07F 11/44* (2013.01); *G07F 17/0092* (2013.01); *G16H 20/13* (2018.01); *A61J 1/03* (2013.01); *A61J 7/0418* (2015.05); *A61J 7/0481* (2013.01); *A61J 2200/30* (2013.01)

(58) Field of Classification Search
CPC .......... A61J 1/03; A61J 7/0076; A61J 7/0445; A61J 7/0481; B65D 83/0409; G06F 19/3462; G07F 17/0092
See application file for complete search history.

(56) References Cited

U.S. PATENT DOCUMENTS

1,974,332 A    9/1934   Hauck
3,129,845 A    4/1964   Musser
(Continued)

*Primary Examiner* — Gene O Crawford
*Assistant Examiner* — Kelvin L Randall, Jr.
(74) *Attorney, Agent, or Firm* — Dentons US LLP (57) ABSTRACT

In an apparatus for dispensing, a dispenser includes a housing, a reservoir housed within the housing, a chute in fluid communication with the reservoir, wherein the chute is adjacent to the reservoir, a user input device, a power source housed within the housing, a logic housed within the housing, wherein the power source powers the logic, a motor housed within the housing, wherein the power source powers the motor, wherein the logic controls the motor, a gear train housed within the housing, wherein the motor drives the gear train, a first platform defining an opening, wherein a portion of the first platform abuts a bottom portion of the chute when the dispenser is in a non-dispensing state, and a second platform including a well, wherein the gear train is configured to rotate the second platform relative to the housing, and wherein when the logic sets the dispenser to a dispensing state a position of the well is adjustable relative to the housing via the user input device, such that the well substantially aligns with the chute.

19 Claims, 8 Drawing Sheets

(51) Int. Cl.
 *G16H 20/13* (2018.01)
 *A61J 1/03* (2006.01)

(56) References Cited

U.S. PATENT DOCUMENTS

| | | | |
|---|---|---|---|
| 3,344,951 A | 10/1967 | Gervais | |
| 3,410,452 A | 11/1968 | Igel et al. | |
| 3,593,881 A | 7/1971 | Paap | |
| 3,638,830 A | 2/1972 | Belokin, Jr. | |
| 3,730,388 A | 5/1973 | Bender | |
| 3,833,147 A | 9/1974 | Borsum et al. | |
| 3,854,626 A | 12/1974 | Krechmar | |
| 4,109,825 A * | 8/1978 | Weitzman | G07F 11/54 221/122 |
| 4,117,956 A | 10/1978 | von Schuckmann | |
| 4,127,190 A | 11/1978 | Sunnen | |
| 4,146,151 A | 3/1979 | Davis | |
| 4,230,236 A | 10/1980 | Boulter | |
| 4,405,060 A | 9/1983 | Hsei | |
| 4,415,098 A | 11/1983 | Haas | |
| 4,457,451 A | 7/1984 | Ichikawa | |
| 4,460,106 A | 7/1984 | Moulding et al. | |
| 4,519,515 A | 5/1985 | Schonberger | |
| 4,573,606 A | 3/1986 | Lewis et al. | |
| 4,648,529 A | 3/1987 | Blakemore et al. | |
| 4,674,651 A | 6/1987 | Scidmore et al. | |
| 4,747,514 A * | 5/1988 | Stone | A61J 7/0481 221/15 |
| 5,097,982 A | 3/1992 | Kedem et al. | |
| 5,127,543 A | 7/1992 | Meisels | |
| 5,267,265 A | 11/1993 | Mizoguchi | |
| 5,368,406 A | 11/1994 | Hanshaw | |
| 5,405,045 A * | 4/1995 | Usmani | A24F 15/005 221/15 |
| 5,460,295 A | 10/1995 | Law | |
| 5,582,323 A | 12/1996 | Kurtenbach | |
| 5,667,097 A | 9/1997 | Joyce | |
| 5,791,515 A | 8/1998 | Khan et al. | |
| 5,816,441 A | 10/1998 | Farside | |
| 6,131,765 A | 10/2000 | Barry et al. | |
| 6,189,731 B1 | 2/2001 | Schmitt | |
| 6,206,235 B1 | 3/2001 | Green | |
| 6,267,265 B1 | 7/2001 | Issa | |
| 6,401,991 B1 | 6/2002 | Eannone | |
| 6,529,446 B1 | 3/2003 | de la Huerga | |
| 6,726,058 B2 | 4/2004 | Giraud | |
| 6,763,971 B1 | 7/2004 | Tong | |
| 6,889,869 B2 | 5/2005 | Hallin | |
| 7,036,681 B2 | 5/2006 | Suda et al. | |
| 7,073,685 B1 | 7/2006 | Giraud et al. | |
| 7,108,153 B2 | 9/2006 | Wood | |
| 7,186,176 B2 * | 3/2007 | Umeda | G07D 1/00 109/47 |
| 7,214,385 B2 | 5/2007 | Gruber | |
| 7,988,016 B2 | 8/2011 | Klein et al. | |
| 8,657,155 B2 | 2/2014 | Dwork et al. | |
| 8,936,175 B1 | 1/2015 | Song | |
| 9,101,531 B1 | 8/2015 | Song | |
| 9,283,150 B2 | 3/2016 | Bujalski et al. | |
| 9,636,279 B2 | 5/2017 | Song et al. | |
| 9,669,989 B2 * | 6/2017 | Sanders | A61J 1/03 |
| 2004/0016763 A1 | 1/2004 | Hilliard | |
| 2004/0045977 A1 | 3/2004 | William et al. | |
| 2005/0205595 A1 | 9/2005 | Lepke et al. | |
| 2007/0228065 A1 | 10/2007 | Anderson et al. | |
| 2009/0223994 A1 * | 9/2009 | Getz | A61J 7/0076 221/154 |
| 2010/0012547 A1 | 1/2010 | Gardner | |
| 2011/0166700 A1 | 7/2011 | Dunn | |
| 2011/0172812 A1 | 7/2011 | Joslyn | |
| 2011/0259910 A1 | 10/2011 | Knudsen | |
| 2013/0116818 A1 | 5/2013 | Hamilton | |
| 2014/0305963 A1 * | 10/2014 | Zonana | B65D 83/0409 221/241 |
| 2015/0151899 A1 * | 6/2015 | Reinhold | B65D 83/0409 221/1 |
| 2017/0079887 A1 * | 3/2017 | Song | B65D 83/0409 |

* cited by examiner

TECHNOLOGIES FOR MEDICINE DISPENSING

TECHNICAL FIELD

This disclosure relates to medicine dispensing.

BACKGROUND

In this disclosure, where a document, an act, and/or an item of knowledge is referred to and/or discussed, then such reference and/or discussion is not an admission that the document, the act, and/or the item of knowledge and/or any combination thereof was at a priority date, publicly available, known to a public, part of common general knowledge, and/or otherwise constitutes any prior art under any applicable statutory provisions; and/or is known to be relevant to any attempt to solve any problem with which this disclosure is concerned with. Further, nothing is disclaimed.

Medical pills are designed for medical uses, such as treating medical symptoms, conditions, or diseases. However, some people, including children and elderly, intake the medical pills for non-medical uses, such as due to addiction, entertainment, curiosity, intoxication, mental incompetence, confusion, forgetfulness, or others. As such, this state of being is undesirable for various reasons, such as overdosing, poisoning, or other forms of drug abuse, which may be health hazardous or even lethal. Further, this state of being potentially exposes others, such as caretakers, pharmacists, hospitals, or educational facilities, to legal liabilities, which can be criminal or civil. Although various technologies exist to reduce such intake, these technologies suffer from various drawbacks, such as inability to schedule pill dispensation, inability for on-demand pill dispensation, inability of dispensation tracking, including remotely, and others, all while minimizing chances of undetected pill container tampering and encouraging independent pill self-dispensation.

SUMMARY

This disclosure at least partially addresses at least one of above inefficiencies. However, this disclosure can prove useful to other technical areas. Therefore, various claims recited below should not be construed as necessarily limited to addressing any of the above inefficiencies.

According to an embodiment of this disclosure, an apparatus comprising: a dispenser including: a housing; a reservoir housed within the housing; a chute in fluid communication with the reservoir, wherein the chute is adjacent to the reservoir; a user input device; a power source housed within the housing; a logic housed within the housing, wherein the power source powers the logic; a motor housed within the housing, wherein the power source powers the motor, wherein the logic controls the motor; a gear train housed within the housing, wherein the motor drives the gear train; a first platform defining an opening, wherein a portion of the first platform abuts a bottom portion of the chute when the dispenser is in a non-dispensing state; and a second platform including a well, wherein the gear train is configured to rotate the second platform relative to the housing, and wherein when the logic sets the dispenser to a dispensing state a position of the well is adjustable relative to the housing via the user input device, such that the well substantially aligns with the chute.

According to an embodiment of this disclosure, a method comprises: loading a pill into a dispenser having a chute; sealing the dispenser with the pill being inside thereof; and loading the chute with the pill.

This disclosure is embodied in various forms illustrated in a set of accompanying illustrative drawings. Note that variations are contemplated as being a part of this disclosure, limited only by a scope of various claims recited below.

BRIEF DESCRIPTION OF DRAWINGS

The set of accompanying illustrative drawings shows various example embodiments of this disclosure. Such drawings are not to be construed as necessarily limiting this disclosure. Like numbers and/or similar numbering scheme can refer to like and/or similar elements throughout.

DETAILED DESCRIPTION OF PREFERRED EMBODIMENTS

This disclosure is now described more fully with reference to the set of accompanying illustrative drawings, in which example embodiments of this disclosure are shown. This disclosure can be embodied in many different forms and should not be construed as necessarily being limited to the example embodiments disclosed herein. Rather, the example embodiments are provided so that this disclosure is thorough and complete, and fully conveys various concepts of this disclosure to those skilled in a relevant art.

Features described with respect to certain example embodiments can be combined and sub-combined in and/or with various other example embodiments. Also, different aspects and/or elements of example embodiments, as disclosed herein, can be combined and sub-combined in a similar manner as well. Further, some example embodiments, whether individually and/or collectively, can be components of a larger system, wherein other procedures can take precedence over and/or otherwise modify their application. Additionally, a number of steps can be required before, after, and/or concurrently with example embodiments, as disclosed herein. Note that any and/or all methods and/or processes, at least as disclosed herein, can be at least partially performed via at least one entity in any manner.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Various terminology used herein is for describing particular example embodiments and is not intended to be necessarily limiting of this disclosure. As used herein, various singular forms "a," "an" and "the" are intended to include various plural forms as well, unless a context clearly indicates otherwise. Various terms "comprises," "includes" and/or "comprising," "including" when used in this specification, specify a presence of stated features, integers, steps, operations, elements, and/or components, but do not preclude the presence and/or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

Example embodiments of this disclosure are described herein with reference to illustrations of idealized embodiments (and intermediate structures) of this disclosure. As such, variations from various illustrated shapes as a result, for example, of manufacturing techniques and/or tolerances, are to be expected. Thus, various example embodiments of this disclosure should not be construed as necessarily limited to various particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, an amorphous material, a ceramic, a glass ceramic, an organic solid, such as wood and/or a polymer, such as rubber, a composite material, a semiconductor, a nanomaterial, a biomaterial and/or any combinations thereof. Any and/or all elements, as disclosed herein, can be and/or include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, opaqueness, luminescence, reflection, phosphorescence, anti-reflection and/or holography, a photo-sensitive coating, an electronic and/or thermal property coating, such as for passivity, insulation, resistance or conduction, a magnetic coating, a water-resistant and/or waterproof coating, a scent coating and/or any combinations thereof. Any and/or all elements, as disclosed herein, can be rigid, flexible, and/or any other combinations thereof. Any and/or all elements, as disclosed herein, can be identical and/or different from each other in material, shape, size, color and/or any measurable dimension, such as length, width, height, depth, area, orientation, perimeter, volume, breadth, density, temperature, resistance, and so forth.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized and/or overly formal sense unless expressly so defined herein.

Furthermore, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" and/or "substantially" refers to a +/−10% variation from a nominal value/term. Such variation is always included in any given value/term provided herein, whether or not such variation is specifically referred thereto.

If any disclosures are incorporated herein by reference and such disclosures conflict in part and/or in whole with this disclosure, then to an extent of a conflict, if any, and/or a broader disclosure, and/or broader definition of terms, this disclosure controls. If such disclosures conflict in part and/or in whole with one another, then to an extent of a conflict, if any, a later-dated disclosure controls.

The device uses a platform or shuttle, moved with an electric motor to move between two states, the user moves an assembly or upper deck which contains both the electric motor and the shuttle or platform between two additional states. These two controls give the device a total of 4 different states that can be achieved through a combination of user input and electrically driven timing. Only the correct sequence of events will allow a pill to be dispensed and at no time during any of the states does the user have access to the pills.

The pills are mechanically separated from the user by means of the assembly or upper deck and the platform or shuttle which provide a physical blockage, the electronics sense that the time limit for dispensing a pill has been reached and a motor is activated. This motor motion moves a platform or shuttle to a location where it can retrieve a pill. The platform or shuttle stays in this position until the user activates a mechanical structure to slide the platform or shuttle and the assembly or upper deck to a location where the platform or shuttle can pick up a pill. This motion to provide for pick up if the pill is accomplished by means of the mechanical structure. At no point of this motion is the user in direct contact with a pill. The pill is now in the platform or shuttle and ready to be dispensed to the user. It is, however, still mechanically separated by the electronically activated platform or shuttle. Only after the electronics sense that a pill has been successfully brought to the "on deck" position does it retract the platform or shuttle and give the user access to the medication.

Figure 1:
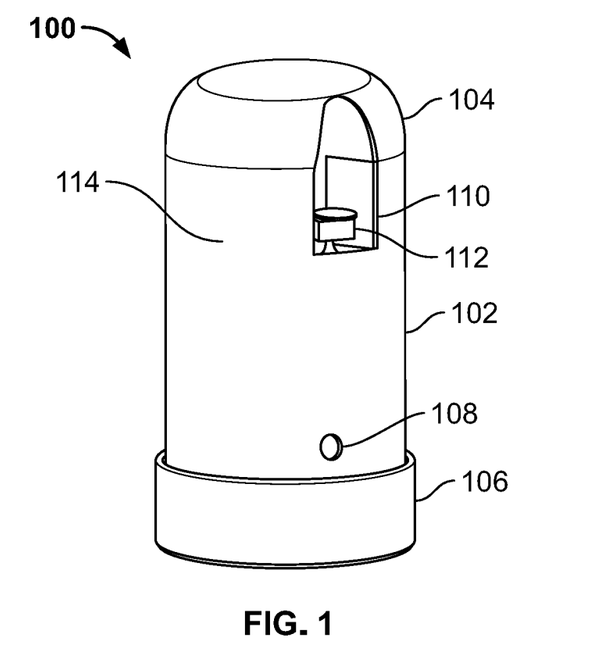
FIG. 1 shows a perspective view of an embodiment of a pill dispenser according to this disclosure.

FIG. 1 shows a perspective view of a pill dispenser according to this disclosure. A pill dispenser 100 includes a tubular cover 102, a dome-shaped cap 104, and an annular base 106, where the cover 102 supports the cap 104 and the base 106 supports the cover 102. The cover 102 includes a sidewall having a visual indicator 108, whether analog or digital, which may switch between at least two states, one state visually indicative of current inability/infeasability to dispense a pill and one state visually indicative of current ability/feasability to dispense a pill. Note that a pill can include a tablet, a capsule, a caplet, or other forms ingestible/digestible medicines. For example, the tablet can be shaped as a round, oval or ovoid disc and the capsule can be shaped as a spherocylinder.

In one or more embodiments, the indicator 108 may be an LED, a colored light, an LCD display or some other type of visual indicator. In one or more embodiments where the indicator 108 is an LCD display, the display includes a portion that identifies the number of pills remaining in an inner reservoir 130, and/or the amount of time remaining until the next dosage may be accessed. This allows patients and/or their caregivers to track their usage and schedule refills for the medication. In one or more embodiments, in addition to or in place of indicator 108, is an audio generator to produces sounds or audible signals that indicate the number of pills remaining in the inner reservoir 130, and/or the amount of time remaining until the next dosage may be accessed. This provides further assistance to patients and/or allows visually impaired patients and/or their caregivers to track their usage and schedule refills for the medication.

The sidewall of the cover 102 contains a transparent or translucent portion 114 extending between the cap 104 and the base 106, where the portion 114 can be of any color. The sidewall of the cover 102 also defines an inward recess 110 in which an input device 112 is user-accessible. As shown in FIG. 1, the input device 112 is a button that is plunged/unplunged along a longitudinal axis of the cover 102 (vertical as shown). However, note that other configurations or other types of the input device 112 are possible, such as the button being depressable/returnable along a lateral axis of the cover 102 or a rotary dial or a slider. Although the recess 110 is shown as being defined via the cap 104 and the cover 102, other configurations are possible, such as only the cover 102 defining the recess 110, or only the cap 104 defining the recess 110.

In one or more embodiments, the cover 102 includes a transparent portion at an area corresponding to the bottom portion of the inner reservoir 130 where the pills are stored. This allows patients and/or their caregivers to track their usage and know when to schedule refills for the medication.

In one or more embodiments, the cover 102 can have a variety of shapes, such as, for example, round, oval, cylindrical, square, rectangular, triangular, polygonal, star shaped or any other shape that corresponds to the shape of the sidewall. In other embodiments, an inner portion of the cover 102 directly above the hole 116 that allows the pills to move from the inner reservoir 130 into the dispensing chute 118 may be curved in a concave shape to act as a funnel to align the pills so that they can more easily load into a chute 118 one by one in a single column.

In one or more embodiments, The base 106 for the pills that have already been dispensed may include a safety cap design that would be child proof.

Figure 2:
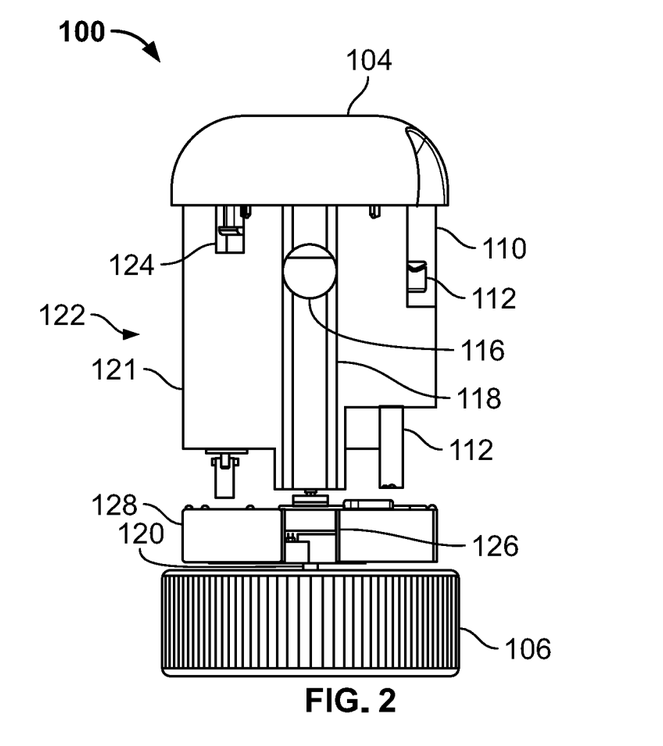
FIG. 2 shows a profile view of an embodiment of a pill dispenser without a tubular cover according to this disclosure.

FIG. 2 shows a profile view of an embodiment of a pill dispenser without a tubular cover according to this disclosure. As the cover 102 is removably detached, the dispenser 100 is shown to have an inner body 122 with a sidewall 123 equipped with a cover interlocker 124 immediately below the cap 104, which is used to removably attach the cover 102 to the inner body 122. Further, the sidewall 121 of the inner body 122 hosts the chute 118 containing a tablet bore 116. The bore 116 is sized such that a pill can pass through the bore 116. The chute 118 is sized to contain one or more pills. The chute 118 is positioned along a longitudinal axis of the body 122 (vertical as shown) between the interlock 124 and the recess 110. Note that the chute 118 and the transparent or translucent portion 114 (as shown in FIG. 1) are co-aligned such that a user can observe, external to the cover 102, whether there are pills in the chute 118, and how many pills are stacked in the chute 118.

The dispenser 100 also includes a platform 128 having a well 126 disposed therein and sized to catchably host a pill received from the bore 116, as the pill transitions from the bore 116 into the well 126, such as, for example, by being dropped, moved, or positioned into the well 126. The platform 128 is positioned between the body 122 and the base 106. The body 122, the platform 128, and the base 106 are mounted onto a rigid shaft 120 extending from the base 106, through the platform 128, and into the body 122. The base 106, the platform 128, and the body 122 are each designed to rotate around, and relative to, the axis formed by the rigid shaft 120.

In one or more embodiments, The cap 106 for the pills that have already been dispensed into well 126 may be a child proof safety cap design.

Figure 3A:
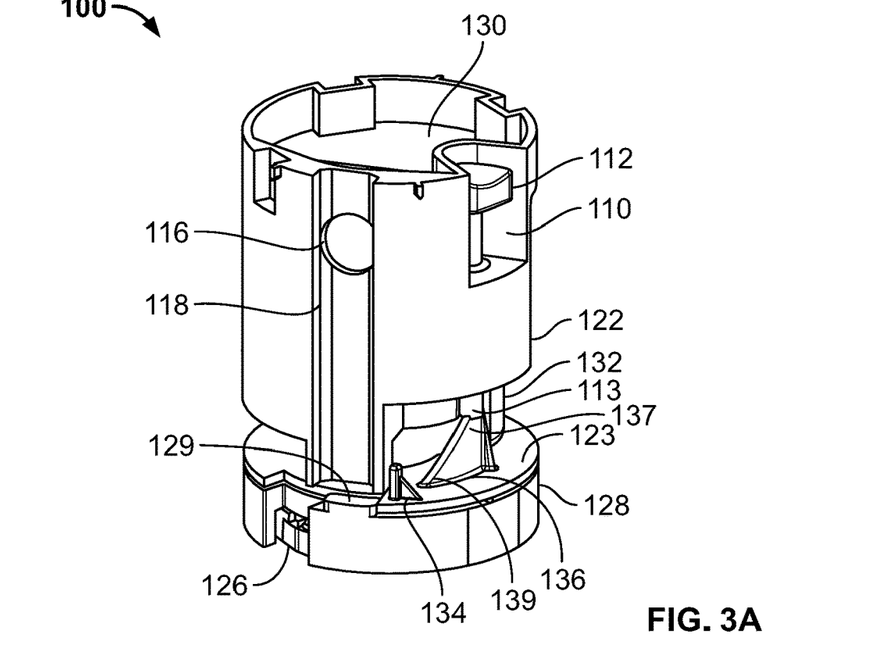
FIGS. 3A-3C show a plurality of perspective views of an embodiment of a pill dispenser without a tubular cover when a chute is not co-aligned with a well of a platform of the pill dispenser and when the chute is co-aligned with the well of the platform of the pill dispenser according to this disclosure.
Figure 3B:
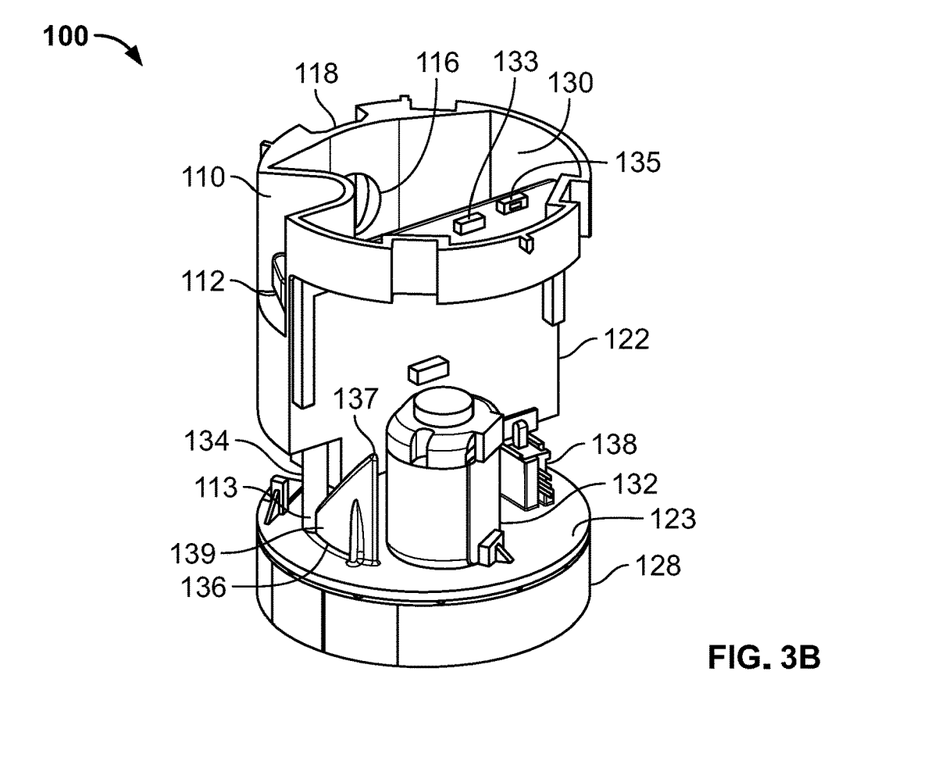
Figure 3C:
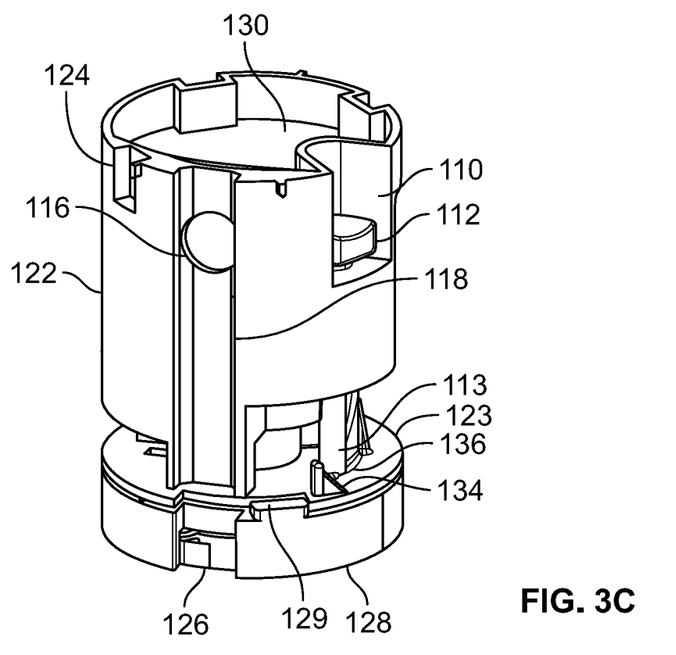

FIGS. 3A-3C show a plurality of perspective views of an embodiment of a pill dispenser without a tubular cover and without a cap. FIG. 3A shows an embodiment when the when a chute is not co-aligned with a well of a platform of the pill dispenser, and FIG. 3C shows an embodiment when the chute is co-aligned with the well of the platform of the pill dispenser according to this disclosure. Similar numbering to the number of FIGS. 1 and 2 are used for FIGS. 3A-3C. The body 122 defines the inner reservoir 130 sized to store a plurality of pills. For example, the number of pills that make up a prescription for a patient can be stored in the inner reservoir 130. This number can be 1 pill, 2 pills, 3 pills, 4 pills, 5 pills, 6 pills, 7 pills, 8 pills, 9 pills, 10 pills, 11, pills, 12 pills, 13 pills, 14 pills, 15 pills, 20 pills, 25 pills, 30 pills, 45 pills, 60 pills, 90 pills, 120 pills, or any other number of pills up to the maximum number of pills that would fit within the inner reservoir 130 leaving sufficient space for the pills to move such that the bore 116 is accessible such that at least one pill can pass through the bore from the inner reservoir 130 to the chute 118. The chute 118 and the inner reservoir 130 are positioned at least one of adjacent one to the other or side-by-side along a longitudinal axis of the body 122 (vertical as shown). As such, when the dispenser 100 is manually shaken, one or more pills in the inner reservoir 130 can exit through the bore 116 and enter into the chute 118 in a stackable manner.

The dispenser 100 includes a platform 128, which includes an upper deck 123. The platform 128 and the upper deck 123 are coupled to the body 122 such that the body 122 can rotate about a vertical axis, which is parallel to the longitudinal axis of the body 122, independently of and with respect to the platform 128 and the upper deck 123 such that the chute 118 can be selectively co-aligned or misaligned with the well 126, and having no partition separating the well 126 from the chute 118. The upper deck 123 supports, including rigidly, an electric motor 132, whether brushed or brushless, and a logic device 138 (as shown in FIG. 3B) controlling the motor 132. The logic device 138 can include a processing circuit/memory with a set of locally executable instructions, which may be reprogrammable, whether locally or remotely, including wirelessly, such as via a transceiver 133.

As shown in FIG. 3B, according to one or more embodiments, the logic device 138, includes a microprocessor and a memory. The memory stores a set of locally executable instructions. The microprocessor is programmable and/or reprogrammable, via a connector 135 located under the cover 102 or cap 104. The connector is accessible after removal of the cover 102 or cap 104. The connector can be any commonly used connector, such as, for example, a micro-USB B, USB Mini-b, or lightning connector. The programming and/or reprogramming is accomplished by connecting a computer or dedicated programming device to the dispenser via the connector. The microprocessor may be programmed and/or reprogrammed directly using the computer or dedicated programming device or via a software program downloaded to the memory. Alternatively, the microprocessor is programmable and/or reprogrammable wirelessly, such as via a wireless connection or network, for example, using a transceiver. The wireless connection or network may be accomplished using WPAN, such as Bluetooth, WLAN, such as WiFi, WMAN, such as WiMAX, or WAN, such as cellular. It is preferable to use a short range connection or network so that the programming can be accomplished only when the dispenser is within a short distance from the programming source. This could limit the ability of a non-approved programming source from programming or reprogramming the dispenser. In one or more embodiments, the dispenser is designed such that the microprocessor may not be programmed or reprogrammed until the cover 102 or cap 104 is removed and/or until a code is entered via the connector or another input device located under the cover 102 or cap 104.

In one or more embodiments, the wireless programming is accomplished via a transceiver 133, which is programmed to receive signals, using a predetermined protocol, that accomplish a programming or reprogramming of the microprocessor directly using a graphical user interface presented on the computer or dedicated programming device or via a software program downloaded to the memory.

The upper deck 123 also supports a stopper column 134 and a ramp track 136 which is engaged by the input device 112. The stopper column 134 is structured to limit counter-clockwise rotational movement of the body 122 independent of the upper deck 123. The ramp track 136 is inclined such that when the input device 112 is not plunged or depressed in the recess 110, as shown in FIG. 3A, then the input device 112 engages an upper portion 137 of the ramp track 136 and the chute 118 is misaligned with respect to the well 126, and an upper portion of the platform 129 acts as a floor to the chute 118. Note that the stopper column 134 limits a range of rotational movement of the body 122 via contactedly resisting further movement against a portion of the body 122 adjacent to the chute 118.

When the input device 112 is manually plunged or depressed in the recess 110, as shown in FIGS. 3B and 3C, then such movement descendably engages the bottom portion 113 of the input device 112 from the upper portion 137 of the ramp track 136 towards a lower portion 139 of the ramp track 136 and thereby generates a force sufficient to coextensively rotate the platform 128 and the upper deck 123 in a counter-clockwise direction towards a position where the chute 118 can be aligned with the well 126, if the well 126 is unlocked and positioned for such alignment. Upon depression of the input device 112, the bottom portion 113 of the input device 112 moves down the ramp track 136, causing the upper deck 123 and the platform 128 to rotate counter-clockwise relative to the body 122, such that the well 126 is re-positioned for alignment with the chute 118 and the upper portion of the platform 129 is shifted so that it no longer acts as a floor to the chute 118. Note that the stopper column 134 is positioned with respect to the portion of the body 122 adjacent to the chute 118 such that the stopper column 134 does not prevent the clockwise rotation of the body 122.

Figure 4A:
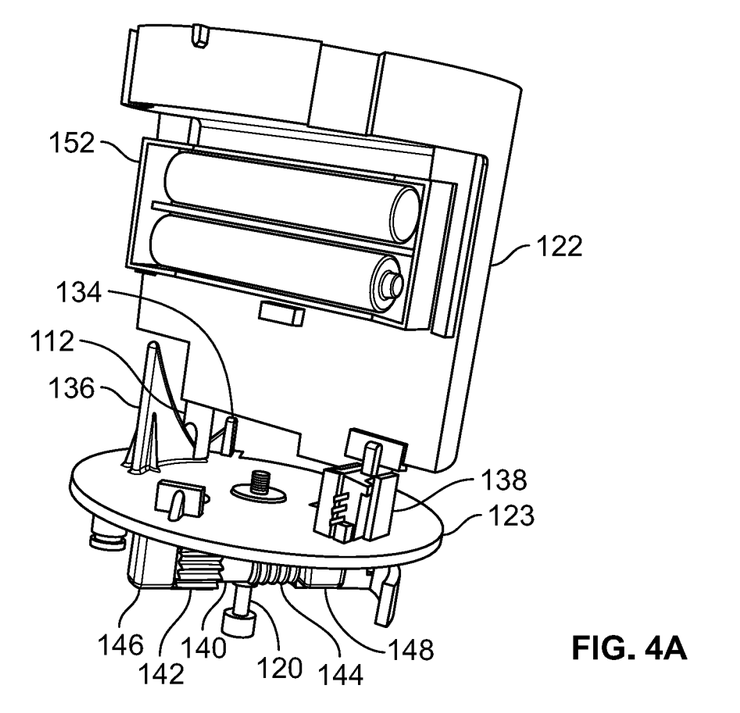
FIGS. 4A-4C show a plurality of perspective views of an embodiment of a pill dispenser with a gear train according this disclosure.
Figure 4B:
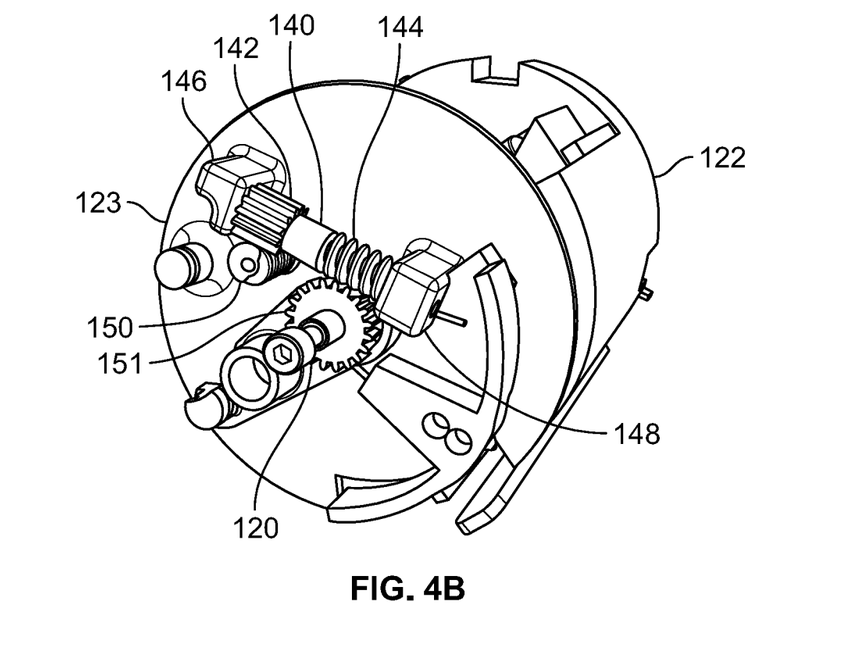
Figure 4C:
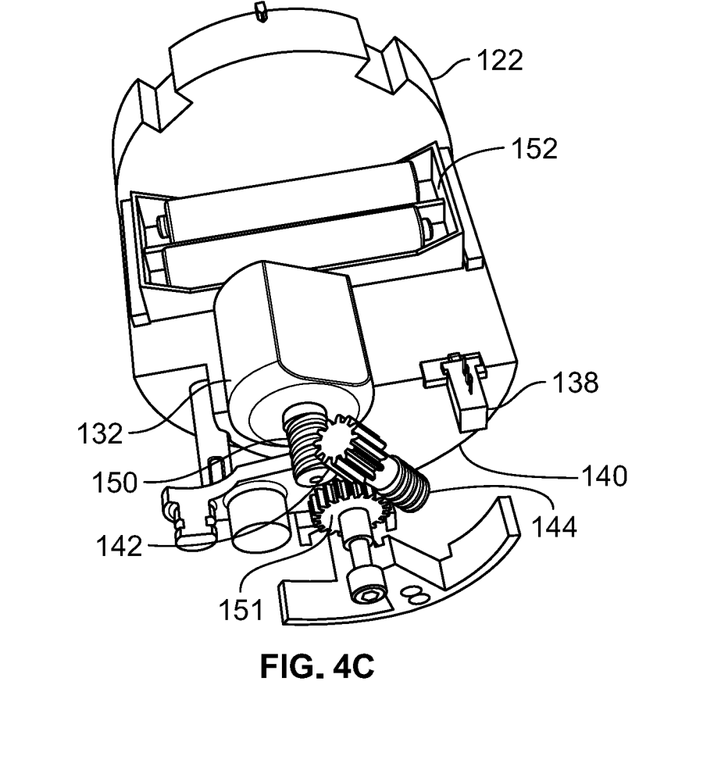

FIGS. 4A-4C show a plurality of perspective views of an embodiment of a pill dispenser with a gear train according to this disclosure. The body 122 hosts a power source 152, such as a pair of batteries, which may be rechargeable, which may be lithium based, although any battery type can be used. The power source 152 powers the motor 132 and the logic device 138.

As shown in FIG. 4A, the upper deck 123 hosts a pair of mounts 146, 148 rigidly coupled thereto. The mounts 146, 148 support a shaft 140 spanning therebetween. The shaft 140 hosts a first worm wheel 142 and a first worm screw 144 on opposing ends thereof. As shown in FIG. 4C, the motor 132 includes a second worm screw 150 engagably meshing with the first worm wheel 142. The shaft 120 extends through the upper deck 123 and has a second worm wheel 151 rigidly mounted thereto and engagably meshing with the worm screw 144.

When the dispenser 100 is inactive, for example, during a time period when medication is not being dispensed, or it is not a dosing time according to a dosing schedule of a patient, the motor activates to rotate the platform 128 in a clockwise direction relative the upper deck 123 and the body 122. This rotation begins from the point where the well 126 is misaligned with the chute 118, and the stopper column 134 is engaged with the body 122 such that the stopper column 134 is contactedly resisting further clockwise movement of the upper deck 123 by abutting against a portion of the body 122 adjacent to the chute 118. The rotation of the platform 128 is caused by the activation of the motor 132 which results in a rotation of the shaft 120, which in turn results in a rotation of the platform 128 via engagement of the first worm wheel 142 with the second worm screw 150 and the second worm wheel 151 with the first worm screw 144. The motor 132 is activated for a time sufficient to rotate the platform 128 in a clockwise direction a distance approximately equal to the width of the well 126. Thus, when the dispenser 100 is in the non-dispensing mode, the well 126 will be positioned in a direction clockwise from the chute 118 a distance of approximately two well 126 lengths from alignment with the chute 118. If the motor 132 is not provided with a signal indicating that it is time to dispense medication, the platform 128 will remain locked in such position relative to the body 122 as a result of the engagement of the worm wheels and worm screws which will prevent movement of the platform 128 relative to the body 122.

When the dispenser 100 is activated, for example, during a time period when a signal indicates that a medication is to be dispensed or available for dispensing, or it is a dosing time according to a dosing schedule of a patient, the motor activates to rotate the platform 128 in a counter-clockwise direction relative the upper deck 123 and the body 122. This rotation begins from the point where the well 126 is misaligned with the chute 118 by approximately twice the width of the well 126. The rotation of the platform 128 is caused by the activation of the motor 132 which results in a rotation of the shaft 120, which in turn results in a rotation of the platform 128 via engagement of the first worm wheel 142 with the second worm screw 150 and the second worm wheel 151 with the first worm screw 144. The motor 132 is activated for a time sufficient to rotate the platform 128 in a counter-clockwise direction a distance approximately equal to the width of the well 126. Thus, when the dispenser 100 is in the dispensing mode, the well 126 will be positioned in a direction clockwise from the chute 118 a distance of approximately one well 126 length from alignment with the chute 118.

Figure 5A:
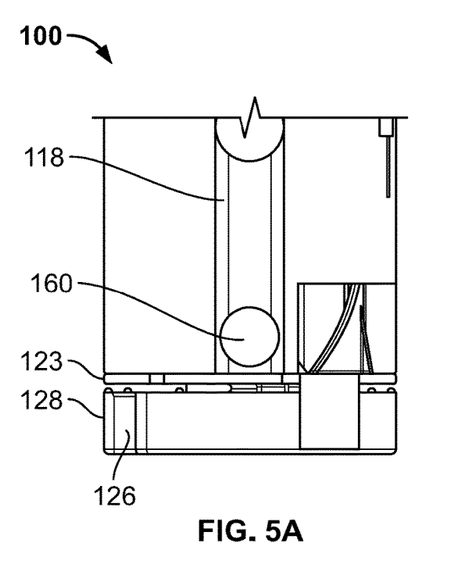
FIGS. 5A-5G show a set of profile views of a set of embodiments of a set of motions of a set of parts of a dispenser according to this disclosure.
Figure 5B:
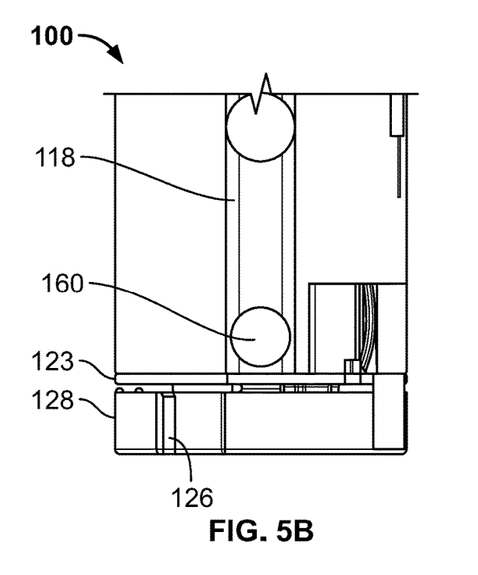
Figure 5C:
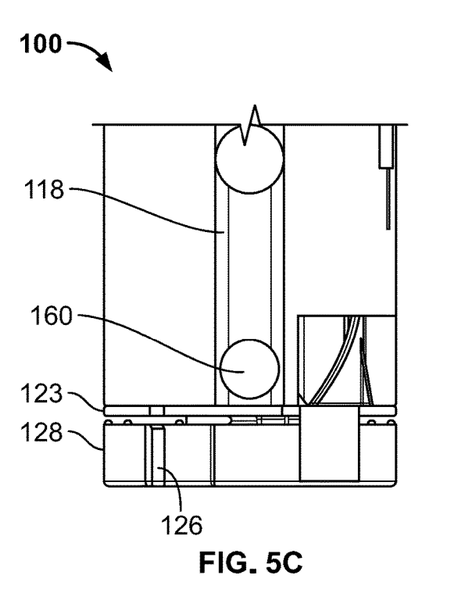
Figure 5D:
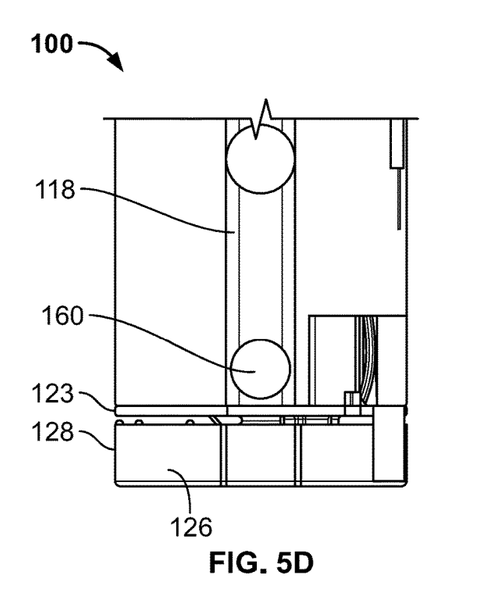
Figure 5E:
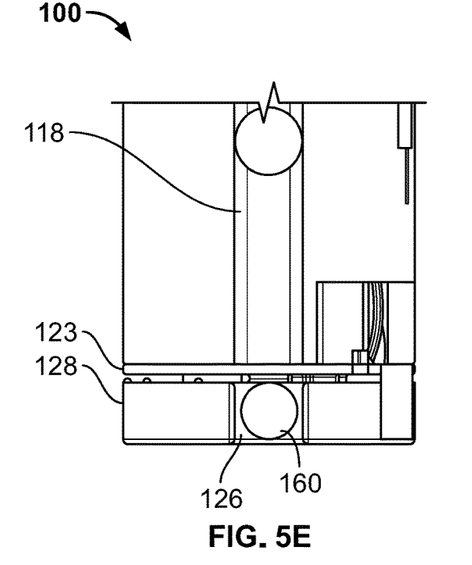
Figure 5F:
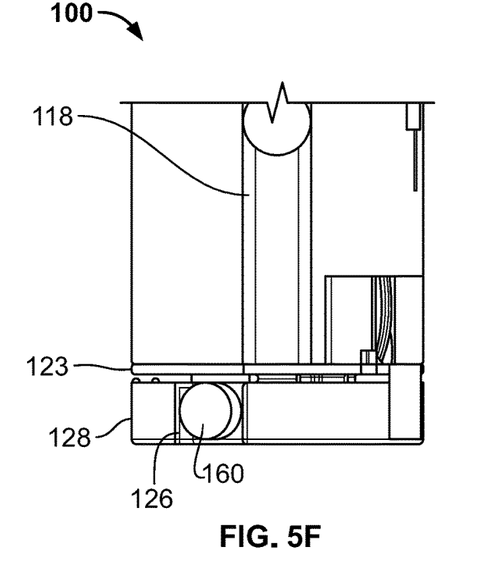
Figure 5G:
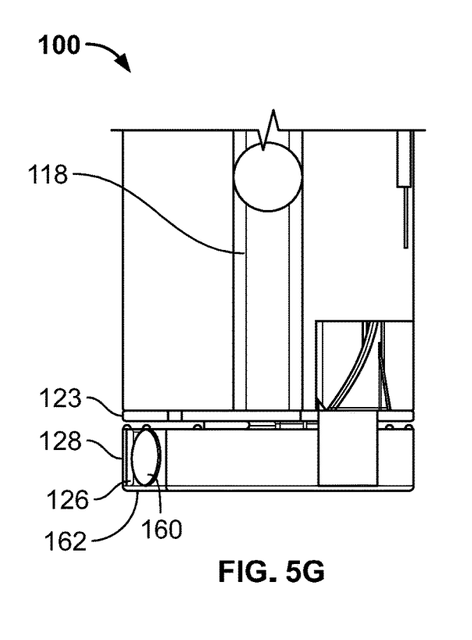
Figure 6:
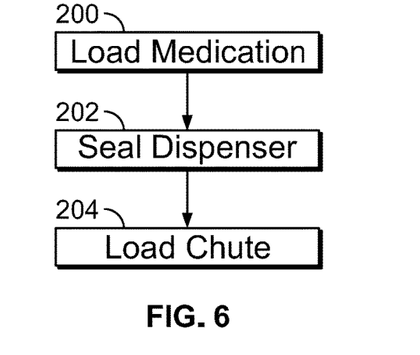
FIG. 6 shows a flowchart of an embodiment of a loading function for a dispenser according to this disclosure.

The dispenser 100 is locked by default. For example any loss of power prevents dispensing of the medications. The dispensing of medications, such as, for example, pills, capsules, tablets, caplets, and/or gel caps, among other forms of medication, is metered by means of an electronically defeatable mechanical lock-out. This approach is unique because the electronics are required for both arming and disarming the mechanical lock out. A failure of the electronics at any point of the dispensing cycle does not give unwanted access to the pills by the user. The motor used in this device also implements a non-back drivable configuration in the form of a worm gear, as shown in FIGS. 4B and 4C as either, or a combination, of the first worm wheel 142, and/or the second worm screw 150, and/or the second worm wheel 151, and/or the first worm screw 144. Any attempts to overpower the motor to gain unwarranted access to the pills would lead to damage of the dispenser 100 which would alert the prescriber to the infraction, and could also activate an alert to notify the pharmacy, pharmacist, physician, medical staff and/or police. The motion of the parts of the dispenser are illustrated in FIGS. 5A-5G. In FIG. 5A, the dispenser 100 is shown in a default position, where the pill 160 is blocked from exiting the dispenser 100 by the platform 128 and the upper deck 123. In this default position, the well 126 is two well lengths away from the chute 118. In FIG. 5B, the dispenser 100 is shown in a position when the user presses the button 112 and it is still not yet time for dispensing a pill. In this position, the well 126 is one well lengths away from the chute 118. In FIG. 5C, the dispenser 100 is in a position when the time for a pill to be dispensed has come. In this position, the well 126 is one well length away from the chute 118. The user is still physically blocked by the upper deck 123, and the platform 128 has moved its position relative to the shuttle carrier and the rest of the assembly. In this position, the dispenser 100 is primed for dispensing the pill 160, subject to the user pressing the button 112. Until the user presses the button 112, the well 126 remains offset from the chute 118 by one well length. FIG. 5D shows the position of the device when it is time for the pill 160 to be dispensed and the user has depressed the button. The user is no longer blocked by the upper deck 123 or the platform 128 from accessing the pill 160. As shown in FIG. 5E, while the button 112 is depressed by the user, the pill 160 will drop from the chute 118 into the well 126. The user is still physically blocked from accessing the pill 160 by the platform, but the pill 160 is "on-deck" and ready to be dispensed. As shown in FIG. 5F, this depicts the dispenser 100 immediately after the pill 160 has dropped into the well 126 and the user is still pressing button 112. The platform 128 cycles back toward the default position, which is not yet reached as a result of the depression of the button 112 by the user, although the platform 128 is now positioned such that the well 126 is one well length out of alignment with the chute 118. As shown in FIG. 5G, when the user lets go of the button 112 after the pill 160 has been moved from the "on-deck" position to the default position, the pill 160 is aligned with and over a hole 162 which allows the pill 160 to be dispensed to the user. The electronics in the dispenser 100 registers the absence of the pill 160 once the pill 160 drops out from the dispenser 100 and counts it as a successful dispensing. The loading function for a dispenser according to one or more embodiments is described in FIG. 6. In step 200, the medication is loaded into the inner reservoir 130 by the pharmacist. In step 202, the medication dispenser is then sealed to prevent undetectable entry. The only button visible to the patient is button 112 which is mechanically operated. The inner reservoir 130, filled with medication, for example, pills, tablets, capsules, caplets, gelcaps, has an opening which connects the inner reservoir 130 to a chute 118 with dimensions sufficient to hold the medication in a vertical stack. In step 204, the patient shakes the dispenser to transfer the medication through the opening and into the chute, where the medication is visible, but inaccessible by the patient.

Figure 7:
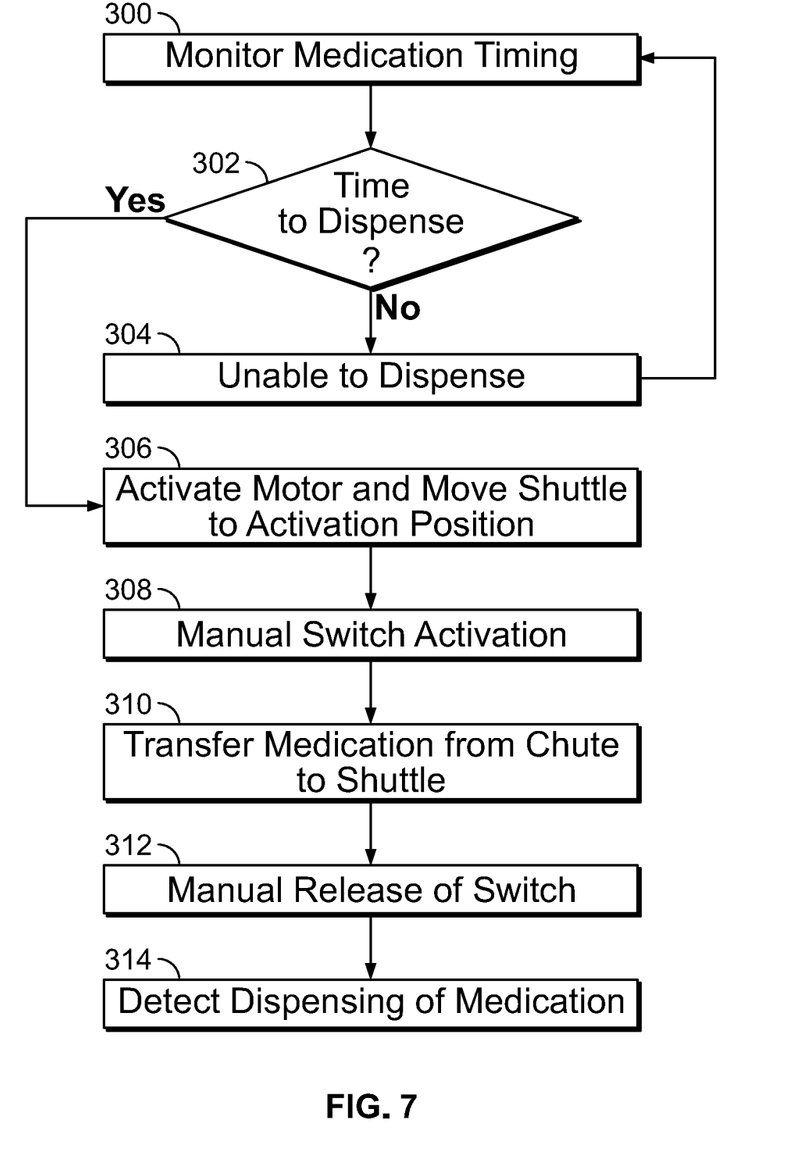
FIG. 7 shows a flowchart of an embodiment of a dispensing function relative to time according to this disclosure.

In one or more embodiments, the dispensing function is gated by a timer, timing circuit or timing program. The dispensing function relative to time is shown in FIG. 7. In step 300, time relative to a patient's medicating requirements is monitored by a timer, timing circuit or timing program embodied in internal electronics and/or a software program connected to an electric motor. The electric motor is connected to a shuttle which rotates back and forth or clockwise and counter-clockwise depending on the time being monitored relative to the patient's medication cycle, prescription or requirements. In step 302 if the timer indicates that it is not yet time to dispense the medication, then at step 304, the patient may press the button without consequences, as the internal dispensing mechanism will be unable to align the shuttle with the chute to transfer the medication to a dispensing slot on the shuttle of the dispenser. In step 302, if the timer determines that it is time to dispense the medication, then in step 306, the timer controls the electronics to turn the motor on to move the shuttle to a position where it can be manually activated by the patient using the button. In step 308, the patient activates the switch, by pressing the switch, which physically rotates the shuttle such that the shuttle is positioned with respect to the chute such that, in step 310, the medication is transferred from the chute into the shuttle. The transfer of the medication results from a gravity feed from the chute into the shuttle. At this point the medication is considered "on deck" and ready to be dispensed to the patient. In step 312, the patient releases the button and, in step 314, the medication that was fed into the shuttle is detected by the device to confirm a successful dispense/count the pill number if it is a multiple pill dose situation.

In one or more embodiments, the shuttle may rotate in a single direction. For example, the shuttle may be controlled by a unidirectional motor that moves the worm gears to rotate the shuttle in only a clockwise or only a counterclockwise direction. The base 106 includes a plurality of wells 126, each of which is offset from the others by a predetermined distance such that upon dispensing of a first pill into a first well 126*a* from the chute 118, a second pill is not yet transferred to a second well 126*b*. After dispensing of the first pill, if the dosage is set for dispensation of a plurality of pills, the platform 128 is rotated by the motor 132 and a second pill is then dispensed into the second well 126*b*. After dispensing of the second pill, the unit remains inactive, and the motor is locked thereby preventing any rotation of the base 106 relative the body 122, thereby preventing dispensing of additional medication. After a preset time period, the motor is again activated for dispensing of the next dosage of the medication into the next well 126*n*. The number of wells 126 will depend on the circumference of the base 106 and the amount of spacing necessary to prevent dispensing of a pill into every other well 126 from the chute 118 prior to the base 106 being positioned so as to allow dispensing of the pill from the filled well 126 to a patient.

In one or more embodiments, based on the structure of the chute, the shuttle and rotation controls, the medication in the stack stays mechanically isolated at all times from the dispensing orifice to the outside of the bottle. Thus, there is no way for the patient to obtain medication in excess of the prescribed and programmed amount. In one or more embodiments, The shuttle that controls the dispensing of the medication has only two possible positions, which are determined by the control program connected to the motor. The shuttle can either be positioned to accept medication from the chute into the well, or the on-deck position (but is not capable of dispensing the medication to the patient) or it can be positioned to dispense the medication that is located in the well or the on deck position (over the dispensing hole leading to the bottom of the bottle and therefore dispensed to the outside of the bottle), but cannot access the chute for receipt of the medication. The position of the shuttle is controlled by the electronics and the motor in the bottle and the software that controls the movement of the motor. The mechanical isolation of the medication while the shuttle is in either position prevents people from dispensing more medication than programmed into the bottle or more than prescribed or intended. The gear train that moves the shuttle is not able to be driven backward, meaning any attempt to force the mechanism back to access more medication than programmed on the bottle, prescribed or intended, will likely damage or destroy the dispensing mechanism and/or the bottle.

The system requires both active use by the patient and objective authorization from the program/electronics to dispense medication which ensures that medication is only dispensed when intended or authorized.

Figure 8:
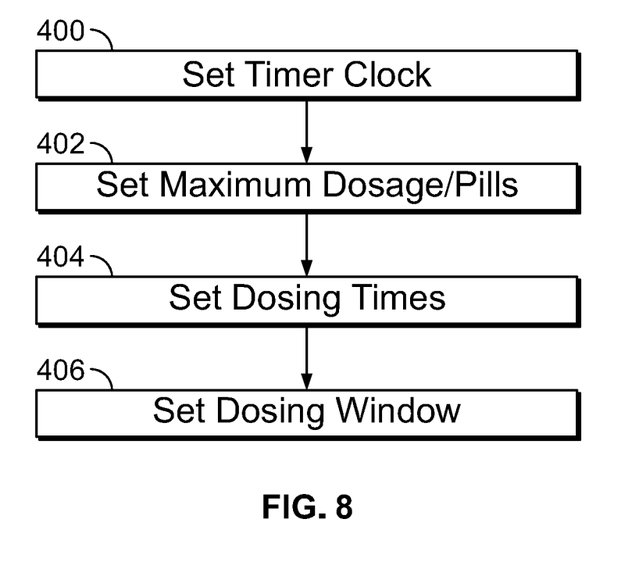
FIG. 8 shows a flowchart of an embodiment of a method of programming a dispenser according to this disclosure.

In one or more embodiments, the dispenser is programmed to dispense medication based on a timed release of a predetermined dosage. An exemplary method for programming the dispenser is set forth in FIG. 8. In step 400 the clock of the timer is set. The timer may be designed in the form of a field programmable gate array, or in the form of a microprocessor programmed to run a timing function. After the clock is set, in step 402, a maximum dosage or number of pills is set. This maximum dosage or number of pills limits the amount of medication that is released by the dispenser when a dosing time is reached. The dosing times are then set, in step 404. This setting of dosage times determines when the motor of the dispenser will be activated to move the shuttle or platform to a release position so that the medication can be dispensed. In step 406 a dosing window is set. This dosing window sets a maximum time that the dispenser will remain in an activated state allowing the dispenser to dispense the medication through interaction by the user. The dosing window may be set to any length of time. In one or more embodiments, the dosing window is set to between around ¼ to around ⅓ of the interval between dosing times. For example, if the dosing spacing is 6 hours, then the dosing window would be set to about 1.5 hours to about 2 hours. That means that from the time the dispenser is activated for release of a dose of medication, the patient would have between around 1.5 to around 2 hours to dispense the medication, or the patient will lose the opportunity to dispense the medication for that dosing period. This time interval allows plenty of time for a patient to access the medication for the dosing period, yet prevents overdosing by maintaining a sufficient spacing between doses, even with such dosing window.

Figure 9:
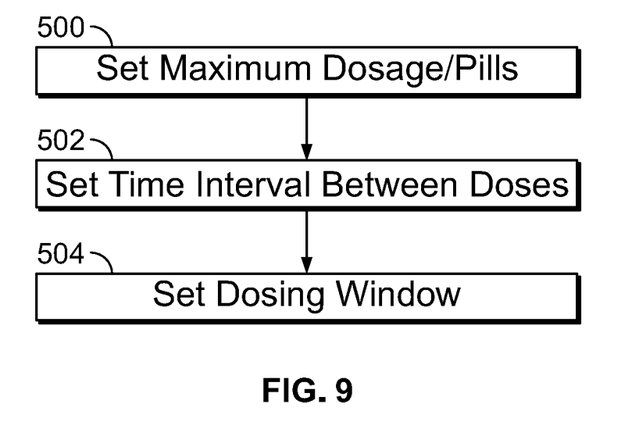
FIG. 9 shows a flowchart of an embodiment of a method of programming a dispenser according to this disclosure.

In one or more embodiments, the dispenser is programmed to dispense medication based on a demand dosing regimen. An exemplary method for programming the dispenser is set forth in FIG. 9. In step 500, a maximum dosage or number of pills is set. This maximum dosage or number of pills limits the amount of medication that is released by the dispenser when a dosing time is reached. The interval time between doses is then set, in step 502. This setting of dosing intervals determines how long after release of the prior dose will the motor of the dispenser will be activated to move the shuttle or platform to a release position so that the next dosage of the medication can be dispensed. In step 504 a dosing window is set. This dosing window sets a maximum time after the dispensing of the first pill of a multi-pill dose of medication that the dispenser will remain in an activated state allowing the dispenser to dispense the final pill of the same dose of medication. The dosing window may be set to any length of time. In one or more embodiments, the dosing window is set to between around ¼ to around ⅓ of the interval between dosing times. For example, if the dosing spacing is 6 hours, then the dosing window would be set to about 1.5 hours to about 2 hours. That means that from the time the dispenser is activated for release of a dose of medication, the patient would have between around 1.5 to around 2 hours to dispense the remaining medication for that same dose, or the patient will lose the opportunity to dispense the medication for that dosing period. This time interval allows plenty of time for a patient to access the medication for the dosing period, yet prevents overdosing by maintaining a sufficient spacing between doses, even with such dosing window.

In one or more embodiments, where indicator 108 on the pill bottle includes a display of a number of pills remaining in the inner reservoir 130, upon each dispending cycle, where a pill is transferred from the chute 118 to the well 126, the number of pills indicated on the indicator 108 will be decreased by one. Alternatively, the number may be decreased only upon the actual dispensing of the pill from the base 106. In one or more embodiments, such tracking of the remaining number of pills is accomplished using one or more sensors 350 positioned in the well(s) 126. The sensor 350 may be positioned in the well 126, and when a pill is transferred into the well 126 from the chute 118, the sensor is activated and will only deduct from the count upon deactivation of the sensor 350 which occurs when the pill is removed from the well 126. This sequential activation and deactivation of the sensor 350 would be the required cycle for deducting from the count on the indicator 108. In one or more embodiments, the sensor determines a presence or absence of an item for dispensing. In one or more embodiments, the presence or absence of the item is determined by determining a change in weight or a change in conductivity.

In one or more embodiments, the inner reservoir 130 incorporates one or more breakable inserts that contains, for example, a colored liquid or gel, a bitter tasting substance, a noxious smelling substance, or an antagonist that would neutralize the medication or inactivate the medication in the inner reservoir 130. Upon improper access to the inner reservoir 130, the insert would break and release the substance into the inner reservoir, where it would coat or interact with the pills in the inner reservoir 130 such that the pills become coated with or wetted by the liquid or gel. This antagonist could be comprised of, for example, a substance that incorporates a medication, such as, for example, naloxone, naltrexone or romazicon that would antagonize the effects of the pills in the reservoir and/or another substance or substances that would make the pills unappealing. One or more of such substances would make the pills unusable. Alternatively, a wall of the inner reservoir 130 itself or the cover 102 could be made to hold such a gel or liquid and release the liquid or gel upon improper access to the inner reservoir 130 of the pill bottle.

In some embodiments, various functions or acts can take place at a given location and/or in connection with the operation of one or more apparatuses or systems. In some embodiments, a portion of a given function or act can be performed at a first device or location, and a remainder of the function or act can be performed at one or more additional devices or locations.

The corresponding structures, materials, acts, and equivalents of all means or step plus function elements in the claims below are intended to include any structure, material, or act for performing the function in combination with other claimed elements as specifically claimed. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the steps can be performed in a differing order or steps can be added, deleted or modified. All of these variations are considered a part of the disclosure. It will be understood that those skilled in the art, both now and in the future, can make various improvements and enhancements which fall within the scope of the claims which follow.

The description of this disclosure has been presented for purposes of illustration and description, but is not intended to be fully exhaustive and/or limited to the disclosure in the form disclosed. Many modifications and variations in techniques and structures will be apparent to those of ordinary skill in an art without departing from a scope and spirit of this disclosure as set forth in the claims that follow. Accordingly, such modifications and variations are contemplated as being a part of this disclosure. A scope of this disclosure is defined by various claims, which include known equivalents and unforeseeable equivalents at a time of filing of this disclosure.

The invention claimed is:

1. An apparatus comprising:
    a dispenser including:
        a housing;
        a reservoir housed within the housing;
        a chute, wherein the chute includes an upper end, a lower end, and a rear wall having an opening therein, wherein the upper end of the rear wall of the chute is adjacent to the reservoir, and wherein the reservoir is in fluid communication with the upper end of the rear wall of the chute via the opening;
        a user input device;
        a power source housed within the housing;
        a logic housed within the housing, wherein the power source powers the logic;
        a motor housed within the housing, wherein the power source powers the motor, wherein the logic controls the motor;
        a gear train housed within the housing, wherein the motor drives the gear train;
        a first platform defining an opening, wherein a portion of the first platform abuts a bottom portion of the chute when the dispenser is in a non-dispensing state; and
        a second platform including a well, wherein the well includes a back wall, two side walls and a bottom, wherein the gear train is configured to rotate the second platform relative to the housing, and wherein when the logic sets the dispenser to a dispensing state a position of the well is adjustable relative to the housing via the user input device, such that the well substantially aligns with the chute.

2. The apparatus of claim 1, wherein the chute is side-by-side to the reservoir.

3. The apparatus of claim 1, wherein the chute is oriented vertically.

4. The apparatus of claim 1, wherein the housing includes a transparent window overlying the chute such that a content of the chute is visible externally to the apparatus.

5. The apparatus of claim 1, further comprising a visual indicator on the housing.

6. The apparatus of claim 5, wherein the visual indicator indicates that the apparatus is in a state such that a content of the apparatus is available for dispensing.

7. The apparatus of claim 6, wherein the visual indicator identifies at least one of a number of pills remaining or a time remaining until the next dispensing.

8. The apparatus of claim 1, wherein the gear train includes a worm gear.

9. The apparatus of claim 1, further comprising a sensor positioned in the well, wherein the sensor determines a presence or an absence of an item for dispensing.

10. The apparatus of claim 9, wherein the determining is accomplished by at least one of determining a change in weight or determining a change in conductivity.

11. The apparatus of claim 1, further comprising a receiver coupled to the logic, wherein the receiver receives a data including a schedule for the dispensing state.

12. The apparatus of claim 1, further comprising a receiver coupled to the logic, wherein the receiver receives a set of instructions directing the logic to dispense according to a predetermined schedule data.

13. The apparatus of claim 12, wherein the receiver only accepts receipt of the set of instructions upon receipt of a predetermined code.

14. The apparatus of claim 12, wherein the receiver is a wireless receiver.

15. The apparatus of claim 1, wherein upon at least one of an access to an inside of the housing, removal of a portion of the housing, or a breach of the housing, a substance is released within the housing.

16. The apparatus of claim 15, wherein the substance is at least one of a permanent die, a neutralizing agent, a substance that makes a dispensed item unappealing, a substance that makes the dispensed item unusable, a noxious smelling substance, or a foul tasting substance.

17. The apparatus of claim 1, wherein the motor may be activated or deactivated, and, when in a deactivated state, the motor prevents rotation of at least one of the first platform or the second platform.

18. The apparatus of claim 1, wherein the gear train comprises a worm gear, and wherein the worm gear prevents rotation of at least one of the first platform or the second platform.

19. The apparatus of claim 1, wherein the motor is at least one of unidirectional or bidirectional.

\* \* \* \* \*